(12) United States Patent
Nonnenmacher

(10) Patent No.: US 8,349,181 B2
(45) Date of Patent: Jan. 8, 2013

(54) FILTER CARTRIDGE, IN PARTICULAR FOR PURIFYING DENTAL WASTE WATERS

(75) Inventor: Eberhardt Nonnenmacher, Ingersheim (DE)

(73) Assignee: Duerr Dental AG (DE)

( * ) Notice: Subject to any disclaimer, the term of this patent is extended or adjusted under 35 U.S.C. 154(b) by 240 days.

(21) Appl. No.: 12/766,117

(22) Filed: Apr. 23, 2010

(65) Prior Publication Data

US 2011/0253615 A1 Oct. 20, 2011

(30) Foreign Application Priority Data

Apr. 14, 2010 (DE) .................. 10 2010 014 949

(51) Int. Cl.
*B01D 36/02* (2006.01)

(52) U.S. Cl. ........ 210/266; 210/282; 210/289; 210/305; 210/307; 210/308; 210/311; 210/315; 210/317; 210/320; 210/456

(58) Field of Classification Search .................. 210/256, 210/259, 261, 262, 304–306, 311, 315, 317, 210/320, 512.1, 266, 282, 289, 308, 309, 210/342, 456
See application file for complete search history.

(56) References Cited

U.S. PATENT DOCUMENTS

| | | | | |
|---|---|---|---|---|
| 74,215 A * | 2/1868 | Gonner et al. | ................. | 210/99 |
| 1,177,174 A * | 3/1916 | Doty | ............................ | 210/130 |
| 3,529,724 A * | 9/1970 | Maciula et al. | ............... | 210/197 |
| 3,585,130 A * | 6/1971 | Gregory | ........................ | 210/266 |
| 3,776,385 A * | 12/1973 | Maciula et al. | ............... | 210/304 |
| 6,331,246 B1 * | 12/2001 | Beckham et al. | ............ | 210/136 |
| 2004/0016691 A1 * | 1/2004 | Smit et al. | ..................... | 210/304 |

FOREIGN PATENT DOCUMENTS

DE 10 2006 012 312 A1 10/2006

* cited by examiner

*Primary Examiner* — Matthew Savage
(74) *Attorney, Agent, or Firm* — Factor Intellectual Property Law Group, Ltd.

(57) ABSTRACT

A filter cartridge, which is suitable in particular for purifying dental waste waters, has a housing with three different spatial regions which receive three different filter materials having different filter properties. The first filter material is preceded by a sedimentation space.

14 Claims, 3 Drawing Sheets

FILTER CARTRIDGE, IN PARTICULAR FOR PURIFYING DENTAL WASTE WATERS

RELATED APPLICATIONS

This application claims the filing benefit of German Patent Application No. 10 2010 014 949.7 filed Apr. 14, 2010, the contents of which are incorporated herein by reference.

TECHNICAL FIELD

The invention relates to a filter cartridge, in particular for purifying dental waste waters, having a housing which comprises a waste water inlet and a pure water outlet, and in the interior space of which at least one filter material is arranged.

BACKGROUND OF THE INVENTION

The laws of different countries govern in different ways the requirements placed on the purity of waste waters fed into the public sewage system in dental practices. In countries with demanding legislation, the required purity of the waste water can only be met with the aid of separating centrifuges. In other countries, the required purity can also be met by sedimentation separators.

It would be desirable to have a separator which, in terms of cost, is significantly below the costs of separating centrifuges, but at the same time has a significantly better separating performance than a pure sedimentation separator.

The present invention is directed to resolving these and other matters.

SUMMARY OF THE INVENTION

The present invention provides a filter cartridge with which a good separating efficiency can be achieved at low cost.

It has been found that a quite good separation of the impurities present in dental waste waters, in particular small amalgam particles, can be achieved by connecting at least two different filter materials in series. A reasonable throughput of the filter is thus still obtained, with operating periods between filter changes lying in the region of 6 months and more, since the pore size of the filter materials is different and the different pore size ensures that both filter materials clog at approximately the same speed.

Since the flow rate in the filter materials or their pores is low, small particles are also retained sufficiently well.

One aspect of the invention is distinguished by a low weight and good adjustability of the pores. A material of this kind is well suited precisely for retaining larger impurities.

In another aspect of the invention, the filter material has a high weight, a dense packing of the individual particles and a good retaining power for impurities. Specifically, it may be a sand filling, similar to sand fillings used for the treatment of drinking water.

In a further aspect of the invention, the filter material is well suited for retaining very fine residual impurities.

According to a further aspect of the invention, the flow passes through a preferred series connection of different filter materials.

In still a further aspect of the invention, the flow passes through very coarse impurities are already separated before they reach the first filter material.

An advantageous aspect of the invention provides the avoidance of swirling and for calming the water flowing into the second filter material. At the same time, it is in this case ensured that the different radial regions of the second filter material receive an equal flow.

Another aspect of the invention provides the benefit of a mechanically simple construction of the filter cartridge.

In a further aspect of the invention the filter cartridge is radially particularly compact.

In yet another advantageous aspect of the invention is attained where, in one embodiment filter cartridge has an axial dimension.

Another further aspect of the invention is advantageous with regard to a simple attachment and detachment of the filter cartridge.

It is to be understood that the aspects and objects of the present invention described above may be combinable and that other advantages and aspects of the present invention will become apparent upon reading the following description of the drawings and detailed description of the invention.

DETAILED DESCRIPTION OF THE PRESENT INVENTION

Figure 1:
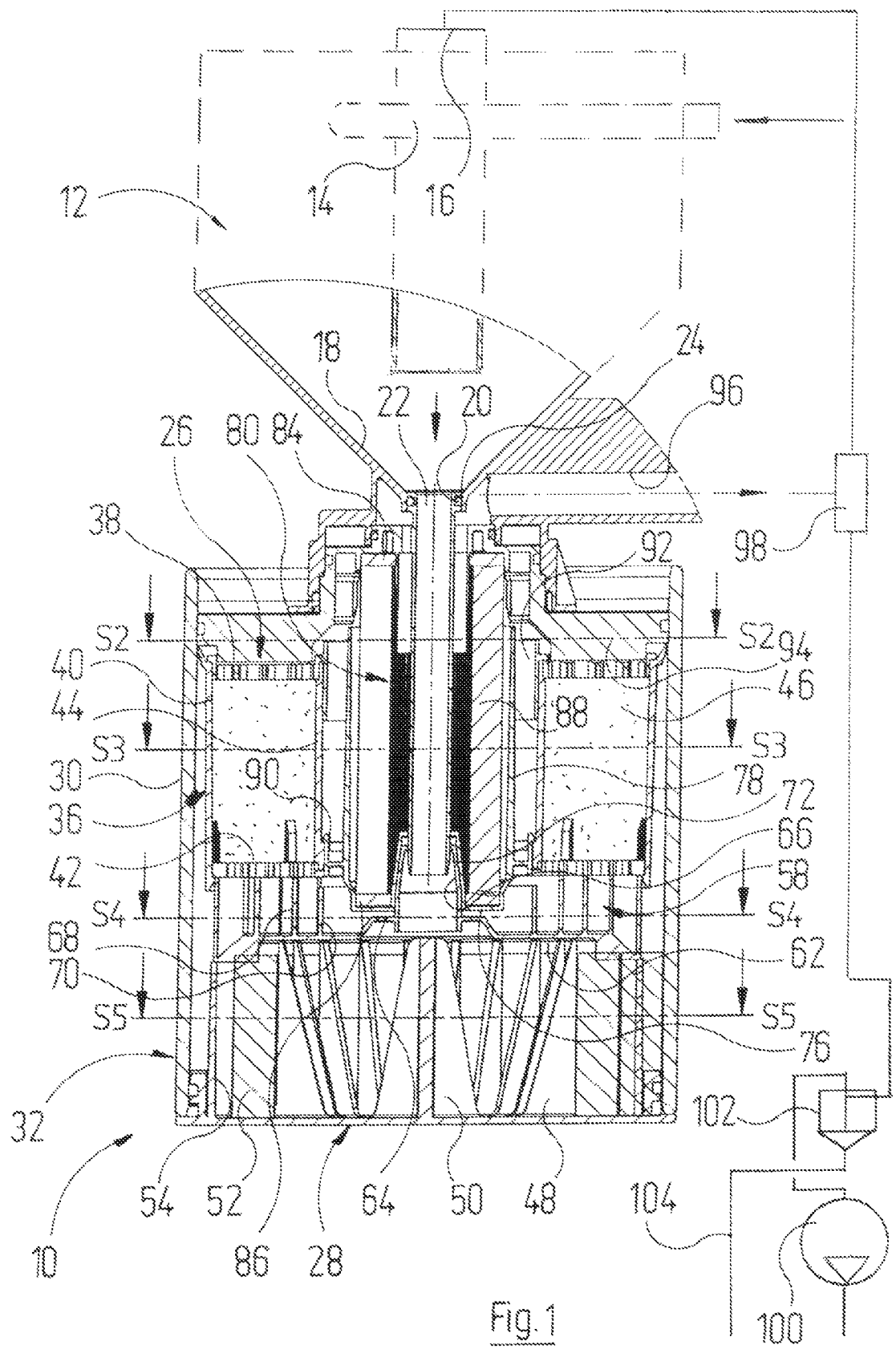
FIG. 1 shows an axial section through a filter cartridge and of the connecting region of an apparatus to which the filter cartridge is connected.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

In FIG. 1, a filter cartridge is denoted as a whole by 10, the filter cartridge being connected to the frustoconical lower end of a cyclone 12, represented merely schematically. Into the cyclone 12 is fed, in a known manner, via a tangential connecting piece 14 a mixture of air, liquid and solid particles which is to be broken down, this mixture arising at a dental workplace, for example being sucked up from a patient's mouth via a suction tube or being discharged from a spittoon.

The connecting piece 14 opens tangentially into the circumferential wall of the cyclone, and liquid and solid constituents are separated from the air by centrifugal action. The air is discharged via an outlet connecting piece 16, and the liquid and solid constituents of the mixture fall into a lower sump section 18 of the cyclone 12.

As shown in FIG. 1, the waste water inlet 22 and the pure water outlet 96 are arranged concentrically on an upper side of the housing.

An inlet pipe 22 of the filter cartridge 10 is connected to the sump section 18 via an O-ring seal 20. This inlet pipe is supported by radial webs 24 by a top part 26 which, together with a bottom part 28 and a circumferential wall 30, constitutes a housing, denoted as a whole by 32, of the filter cartridge 10.

The top part 26 is provided, on its bottom side, with an outer groove 34 which supports an upper filter pot 36. The filter pot 36 for its part consists of a slotted-perforated top 38, a circumferential wall 40 and a slotted-perforated bottom 42. Together with an inner circumferential wall 44, the pot components 38, 40, 42 bound an annular filter space, in which a schematically indicated sand filling 46 is situated.

In a lower region of the housing 32 there are provided equidistant calming vanes 48, which are triangular when seen in the circumferential direction and are integrally formed on the bottom part 28. The calming vanes 48 have axially parallel outer edges and obliquely inwardly sloping inner edges.

In the interior of the ring formed by the calming vanes 48 there are located here furthermore calming vanes 50, which are triangular when seen in the circumferential direction and the radially inner edges of which are connected to one another, while their radially outer edges slope obliquely outwards.

Figure 5:
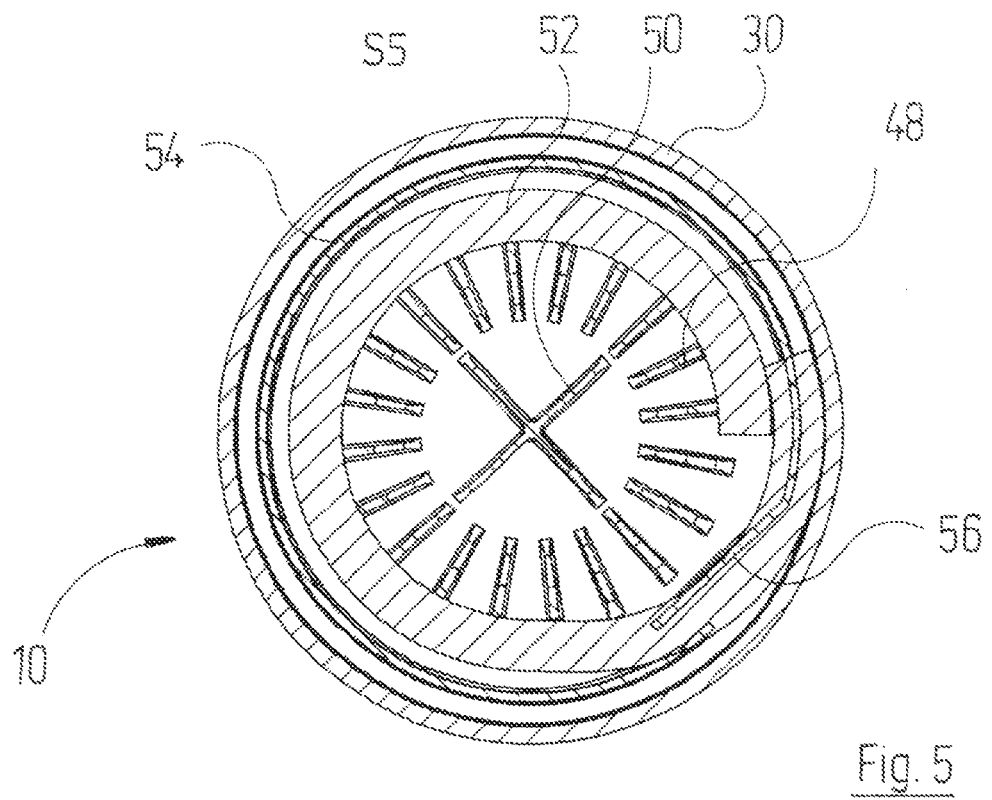
FIG. 5 shows a transverse section through the filter cartridge according to FIG. 1 along the section line S5-S5 therein.

The axially parallel outer edges of the calming vanes 48 support the inner side of a filter foam strip 52 which, as can be seen in FIG. 5, extends circularly over approximately 270°. Over the rest of the circumference, the filter foam strip 52 then runs spiral-like, so that an outer end section overlaps the inner beginning of the filter foam strip 52.

As shown in FIG. 1, in a lower section of the housing the first filter material 52 is arranged in an annular configuration around a first lumen, wherein a sedimentation region which precedes the first filter material is arranged in the first lumen, and wherein the second filter material 46 is arranged in an upper section of the housing and fills an annular space around a second lumen, and wherein a third filter material 60, which is the third through which the flow passes, is arranged in the second lumen.

Radially outside the filter foam strip 52, a partition wall 54 is integrally formed on the bottom part 28 and runs over approximately 300° concentrically with respect to the cartridge axis. A starting section 56, as well as an adjacent cylindrical section running over approximately 30°, of the partition wall 54 is embedded in the filter foam strip 52, the whole in such a manner that the ends of the partition wall 54 overlap slightly in the circumferential direction, but are radially spaced, as can be seen in FIG. 5.

A dish-shaped baffle part 58 is arranged in a central portion of the housing. The upper ends of the calming vanes 48 are integrally formed on the dish-shaped baffle part 58 and support the baffle part 58 in the housing. The latter has a border region 60 which covers over the top side of the filter foam strip 52, a horizontal dish bottom 62 and a central upwardly projecting bottom section 64 which supports a coupling part 66 which is cylindrical at the bottom and frustoconical at the top. The coupling part 66 has at its upper end an inlet opening which engages over the outer surface of the inlet pipe 22 with slight play.

Figure 4:
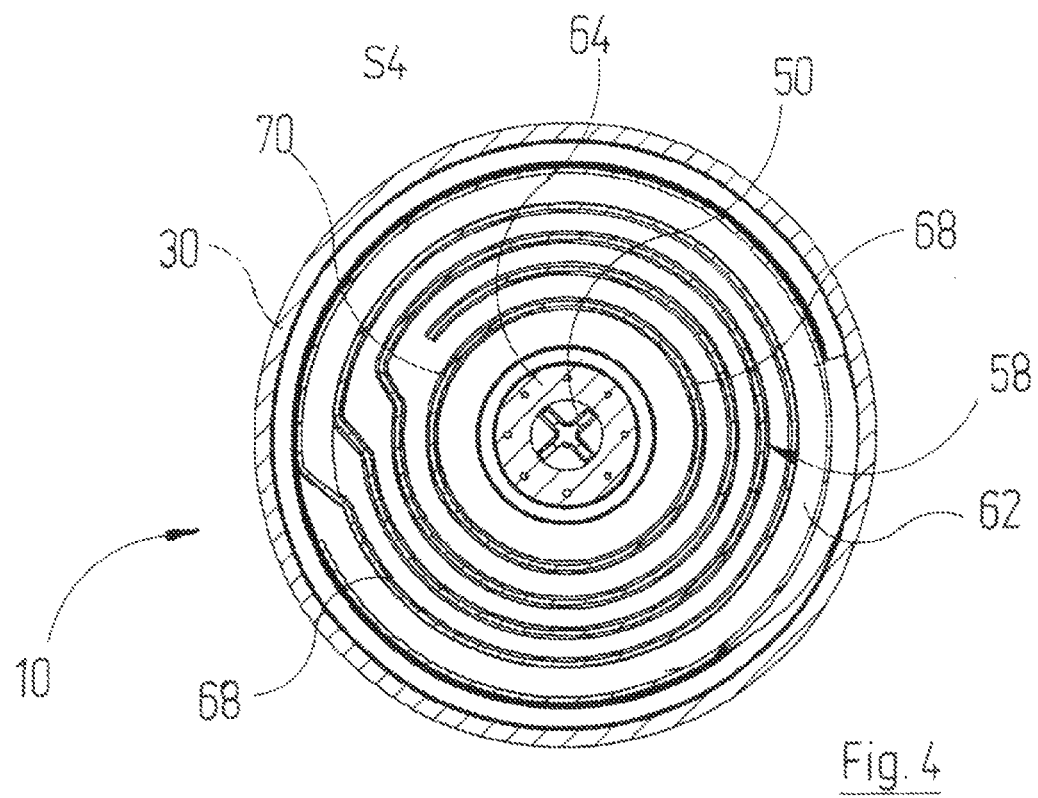
FIG. 4 shows a transverse section through the filter cartridge according to FIG. 1 along the section line S4-S4 therein.

On the top side of the dish bottom 62 there is provided a spiral-shaped calming wall 68, the geometry of which can be seen clearly in FIG. 4. Radially inside the calming wall 68 there is further provided a cylindrical wall 70 which ends with axial spacing below the bottom part 28, while the upper edges of the calming wall 68 extend as far as the bottom side of the bottom part 28.

The coupling part 66 is seated in a complementarily conical coupling part 72 which is integrally formed on a bottom wall 74 of an inner filter housing 76.

Figure 2:
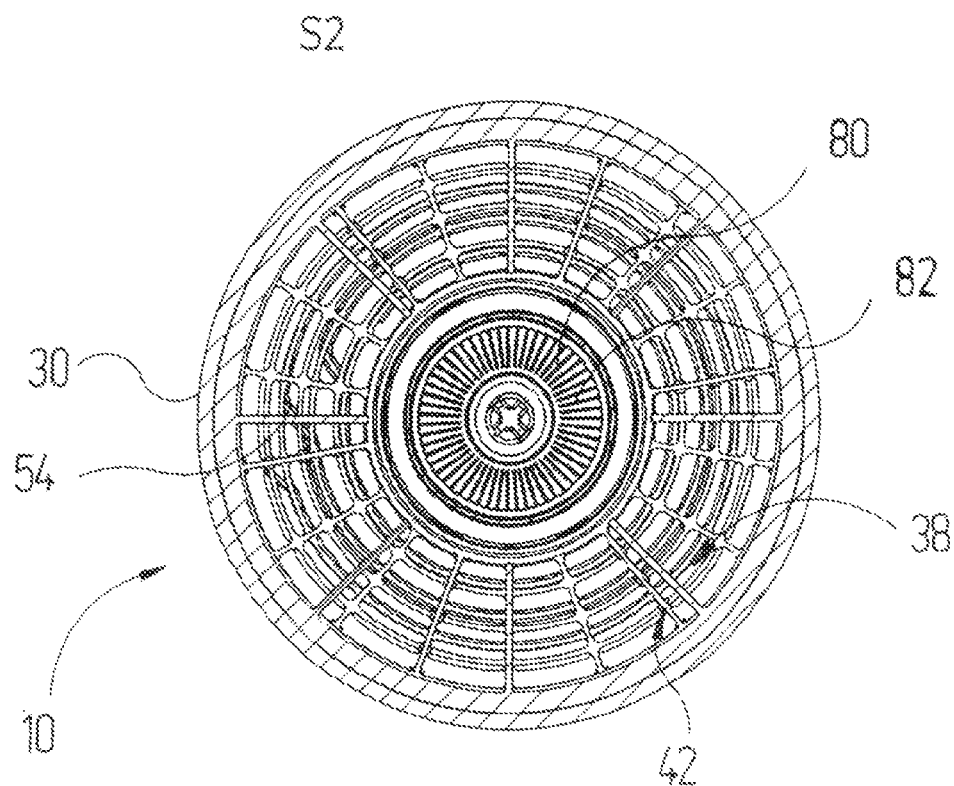
FIG. 2 shows a transverse section through the filter cartridge along the line S2-S2 of FIG. 1.
Figure 3:
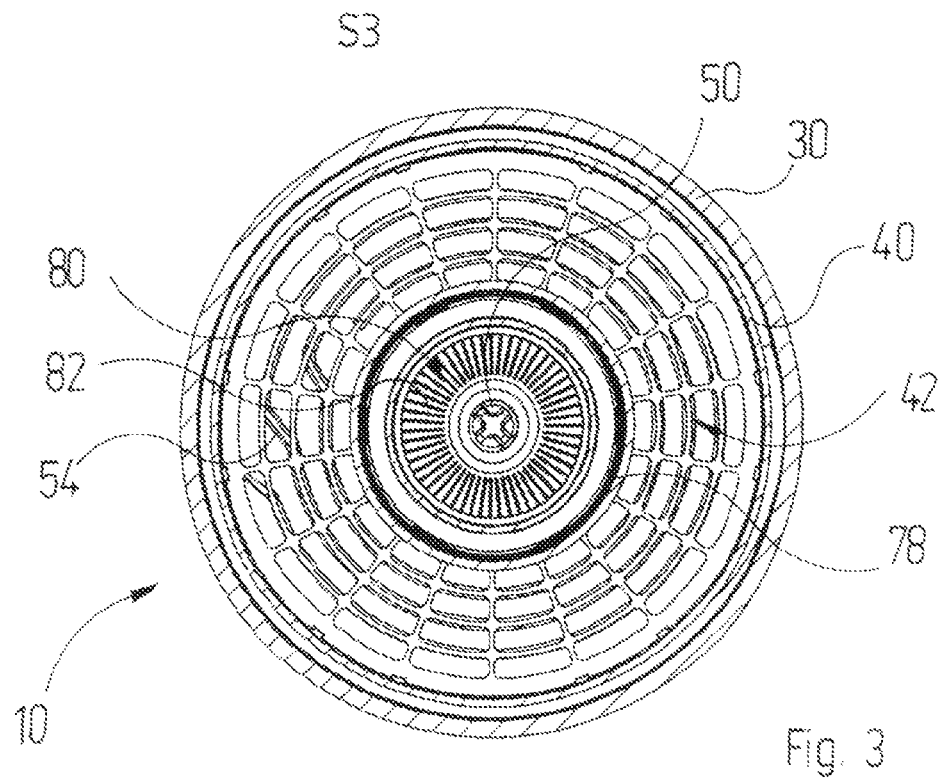
FIG. 3 shows a transverse section through the filter cartridge along the section line S3-S3 of FIG. 1.

The filter housing 76 has an outer pipe section, in the interior space of which a folded paper filter 80 is inserted. The latter has folds 82, which can be seen clearly in FIGS. 2 and 3, and holding rings 84 and 86, respectively, are integrally formed on the upper end of the folded filter paper web.

The paper filter 80 is provided radially inside a star of supporting arms 88, between which liquid can pass to the outer side of the folded paper filter 80.

The filter housing 76 can be connected via latching fingers 90 to the inner circumferential wall 44 of the filter pot 36, as can be seen in the drawing.

The filter housing 76 is centered on the cartridge axis at the upper end by a ring of arms 92 which is connected to the upper end of the inner circumferential wall 44 of the filter pot 36, as can be seen in FIG. 1.

The above-described filter cartridge 10 operates as follows:

Waste water, still comprising solid particles, which arrives in the sump section 18 falls under gravity through the inlet pipe 22 onto the calming vanes 50. Coarse impurities in the supplied waste water settle in the calming space located radially inside the filter foam strip 52, and the water presettled by sedimentation then flows through between the calming vanes 48 and against the inner side of the filter foam strip 52. It then leaves the filter foam strip 52 via the outer surface thereof and rises to the baffle part 58. There, it then flows in a radial inward direction on a spiral-shaped path between the individual windings of the calming wall 68.

The water then enters the sand filling 46 through the perforated bottom part 42, rises in this sand filling 46 and then leaves it via the perforated top part 38.

From the top side of the top part 26, the water then flows through radial slots 94 into the inlet space of the filter housing 76, which space is bounded by the pipe section 78. It then flows through between the supporting arms 88 to the outer surface of the paper filter 80 and then flows axially upwards in the interior of the latter, where it flows via the webs 24 to an outlet duct 96 which is provided in an attachment of the lower section of the cyclone housing.

The purified waste water which has arrived in the outlet duct 96 is then removed by a separate pump. An injector 98 which is operated by the air sucked in from the cyclone 10 by a suction machine 100 can also be used as a pump.

Provided before the inlet of the suction machine 100 is a liquid separator 102 which separates the entrained liquid, which is then discharged to a sewer via a line 104.

For the various filter materials used in the filter cartridge 10, the following materials and pore sizes are typical:

The film foam strip 52 is an open-pored material which is known by the name "structural foam", preferably made of polyester or polyurethane ester. Its pore size is typically 0.5 to 0.8 mm.

The sand filling 46 consists of silica sand having a typical particle size of 1 to 2 mm.

The filter paper 80 is a plastic-reinforced filter paper having a typical pore size of 5 μm The various parts of the housing and of the internal fittings of the filter cartridge 10 are plastic injection-moulded parts.

The filter cartridge 10 is supplied together with a cover which can tightly seal the waste water inlet and the pure water outlet of the filter cartridge simultaneously and roughly speaking has the same geometry as the connecting section of the cyclone 12, with the difference that the waste water inlet from the cyclone is sealed, as is the pure water outlet duct 96.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A filter cartridge for purifying a flow of dental waste waters comprising:
   a housing which comprises a waste water inlet and a pure water outlet,
   wherein the housing has in an interior space in which a first filter material and a second filter material are arranged that are flow-connected in series,
   wherein the first filter material and the second filter material have different filter properties,
   wherein between the first filter material, through which the flow passes first, and the second filter material, through which the flow passes second, there is arranged a baffle part, and,
   wherein the baffle part comprises a dish-shaped bottom and a calming wall on a top side of the dished-shaped bottom, the calming wall contacting a bottom wall that supports the second filter material, wherein the calming wall, together with the bottom wall supporting the second filter material, and the dish-shaped bottom define a path extending parallel to the bottom wall supporting the second filter material so that waste water flowing from the first filter material into the path is allowed to enter the second filter material through the bottom wall supporting the second filter material.

2. The filter cartridge of claim 1, wherein the bottom wall supporting the second filter material is completely covered by the path.

3. The filter cartridge of claim 1, wherein one of the filter materials is an open-pored foam material.

4. The filter cartridge of claim 1, wherein one of the filter materials is a particulate filling.

5. The filter cartridge of claim 1, wherein the first filter material is an open-pored foam material, the second filter material is a particulate filling, and a third filter material arranged in the housing and flow-connected in series with the second filter material, wherein the third filter material is the third through which the flow passes and is a paper filter material.

6. The filter cartridge of claim 1, wherein the first filter material is preceded by a sedimentation region which includes calming vanes.

7. The filter cartridge of claim 6, wherein in a lower section of the housing the first filter material is arranged in an annular configuration around a first lumen, wherein the sedimentation region which precedes the first filter material is arranged in the first lumen, and wherein the second filter material is arranged in an upper section of the housing and fills an annular space around a second lumen, and wherein a third filter material, which is the third through which the flow passes, is arranged in the second lumen.

8. The filter cartridge of claim 6, wherein the baffle part is supported by upper ends of the calming vanes.

9. The filter cartridge of claim 1, wherein the baffle part is arranged in a central region of the housing.

10. The filter cartridge of claim 1, wherein the waste water inlet and the pure water outlet are arranged concentrically on an upper side of the housing.

11. A filter cartridge for purifying dental waste waters comprising:
    a housing which comprises a waste water inlet and a pure water outlet, and
    an interior space containing at least two sub-regions, wherein each sub-region contains a filter material, the filter materials in the sub-regions having different filter properties, and wherein the at least two sub-regions are flow-connected in series,
    wherein between the filter material which is a first through which the flow passes and the filter material which is a second through which the flow passes there is arranged a baffle part which comprises radially nested but, in a circumferential direction, a calming wall defining a flow path having the shape of a spiral.

12. The filter cartridge of claim 11, wherein in a lower section of the housing the filter material, which is the first through which the flow passes, is arranged in an annular configuration around a first lumen, wherein a sedimentation region which precedes the filter material, which is the first through which the flow passes, is arranged in the first lumen, and wherein the filter material, which is the second through which the flow passes, is arranged in an upper section of the housing and fills an annular space around a second lumen, and wherein a filter material, which is the third through which the flow passes, is arranged in the second lumen.

13. The filter cartridge of claim 11, wherein the baffle part is arranged in a central region of the housing.

14. A filter cartridge for purifying dental waste waters comprising:
    a housing which comprises a waste water inlet and a pure water outlet, and
    an interior space containing first, second, and third filter materials having different filter properties, and wherein the first, second, and third filter materials are flow-connected in series,
    wherein the first filter material, which is a first through which the flow passes, is an open-pored foam material,
    wherein the second filter material, which is a second through which the flow passes, is a particulate filling, and,
    wherein the third filter material, which is a third through which the flow passes, is a paper filter material, and,
    wherein in a lower section of the housing the first filter material is arranged in an annular configuration around a first lumen,
    wherein a sedimentation region is arranged in the first lumen,
    wherein the second filter material is arranged in an upper section of the housing and fills an annular space around a second lumen, and
    wherein the third filter material is arranged in the second lumen.

* * * * *